United States Patent
Tsuruta et al.

(10) Patent No.: US 9,902,683 B2
(45) Date of Patent: Feb. 27, 2018

(54) HIGHLY DURABLE POLYESTER POLYOL

(71) Applicant: KURARAY CO., LTD., Kurashiki-shi (JP)

(72) Inventors: Takuo Tsuruta, Tainai (JP); Shigeru Okano, Kamisu (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

(21) Appl. No.: 15/301,184

(22) PCT Filed: Mar. 27, 2015

(86) PCT No.: PCT/JP2015/059686
§ 371 (c)(1),
(2) Date: Sep. 30, 2016

(87) PCT Pub. No.: WO2015/152066
PCT Pub. Date: Oct. 8, 2015

(65) Prior Publication Data
US 2017/0022143 A1  Jan. 26, 2017

(30) Foreign Application Priority Data
Mar. 31, 2014  (JP) ................................ 2014-072677

(51) Int. Cl.
| | | |
|---|---|---|
| C07C 69/013 | (2006.01) |
| C08G 63/18 | (2006.01) |
| C08G 63/199 | (2006.01) |
| C08G 18/42 | (2006.01) |
| C08G 18/66 | (2006.01) |
| C08G 18/76 | (2006.01) |

(52) U.S. Cl.
CPC .......... *C07C 69/013* (2013.01); *C08G 18/423* (2013.01); *C08G 18/4205* (2013.01); *C08G 18/4238* (2013.01); *C08G 18/664* (2013.01); *C08G 18/7671* (2013.01); *C08G 63/18* (2013.01); *C08G 63/199* (2013.01)

(58) Field of Classification Search
CPC .... C07C 69/013; C08G 18/423; C08G 18/42; C08G 63/199; C08G 18/4205; C08G 63/18
See application file for complete search history.

(56) References Cited

U.S. PATENT DOCUMENTS

| | | | |
|---|---|---|---|
| 3,833,665 A | 9/1974 | Papa et al. | |
| 5,118,780 A * | 6/1992 | Hirai | C08G 18/4238 524/265 |
| 6,660,825 B1 | 12/2003 | Endo | |

FOREIGN PATENT DOCUMENTS

| | | |
|---|---|---|
| JP | 47-34494 | 11/1972 |
| JP | 48-28598 | 4/1973 |
| JP | 48-101496 | 12/1973 |
| JP | 5-262869 A * | 10/1993 |
| JP | 6-123007 A * | 5/1994 |
| JP | 7-179555 A * | 7/1995 |
| JP | 10-77325 A | 3/1996 |
| JP | 2002-69163 A | 3/2002 |
| JP | 2002-338650 A * | 11/2002 |
| JP | 2009-13391 A | 1/2009 |
| JP | 2010-235811 A | 10/2010 |
| JP | A-2013-010816 | 1/2013 |

OTHER PUBLICATIONS

Written Opinion dated Jun. 23, 2015 in PCT/JP2015/059686 (with English translation).
International Search Report dated Jun. 23, 2015 in PCT/JP2015/059686 Filed Mar. 27, 2015.
Extended European Search Report dated Nov. 3, 2017, in EP-EESR 15774181.0.
Office Action dated Dec. 5, 2017, in Chinese Patent Application No. 201580017622.8.

* cited by examiner

*Primary Examiner* — Rabon Sergent
(74) *Attorney, Agent, or Firm* — Oblon, McClelland, Maier & Neustadt, L.L.P.

(57) ABSTRACT

A polyester polyol from which a polyurethane having acid resistance and alkali resistance can be produced. A polyester polyol containing 1,3-propandiol having an alicyclic skeleton in a side chain, 3-methyl-1,5-pantanediol, and a dibasic acid component as constituent components.

12 Claims, No Drawings

HIGHLY DURABLE POLYESTER POLYOL

TECHNICAL FIELD

The present invention relates to a polyester polyol from which a highly durable and flexible polyurethane can be produced, a method for producing a polyurethane and a polyurethane.

BACKGROUND ART

Polyurethanes are used in the fields of paints, adhesives, coatings, elastomers, artificial leather/synthetic leather, foams, resins cured by activation energy rays and the like and are useful resins with a wide range of uses.

In general, polyurethanes are known to have various characteristics depending on the structure of the constituent polyol. A polyester polyol containing 3-methyl-1,5-pentanediol as a diol component is highly useful because a polyurethane having excellent flexibility and excellent hydrolysis resistance can be obtained (PTL 1 and PTL 2).

CITATION LIST

Patent Literature

PTL 1: JP-A-47-34494
PTL 2: JP-A-48-101496

SUMMARY OF INVENTION

Technical Problem

Problems of acid rain, salt damage and the like have been drawing attention recently. Thus, as the performance of polyurethanes, improvement of environmental resistance in addition to flexibility and hydrolysis resistance has been required, and polyurethanes are desired to have also excellent acid resistance and excellent alkali resistance. The present inventors have tested the acid resistance and the alkali resistance of the polyester polyol containing 3-methyl-1,5-pentanediol as a diol component and confirmed that there was room for further improvement.

Therefore, objects of the invention are to provide a novel polyester polyol and to provide a polyurethane having excellent acid resistance and excellent alkali resistance using the polyester polyol.

Solution to Problem

As a result of close investigation, the inventors have found that when a polyester polyol contains a specific diol having an alicyclic skeleton in a side chain together with 3-methyl-1,5-pentanediol as diol components, a polyurethane obtained from the polyester keeps the flexibility and the hydrolysis resistance and at the same time has improved acid resistance and improved alkali resistance. Thus, the inventors have completed the invention.

That is, the invention provides [1] to [5] below.
[1] A polyester polyol containing 1,3-propanediol having an alicyclic skeleton in a side chain, 3-methyl-1,5-pentanediol and a dibasic acid component as constituent components.
[2] The polyester polyol described in [1], which has a ratio of use amount of the 1,3-propanediol having an alicyclic skeleton in a side chain and the 3-methyl-1,5-pentanediol of a range of 1/99 to 99/1 by molar ratio.
[3] The polyester polyol described in [1] or [2], wherein the 1,3-propanediol having an alicyclic skeleton in a side chain is cyclohexane-1,1-dimethanol.
[4] A method for producing a polyurethane by reacting the polyester polyol described in any one of [1] to [3] and a polyisocyanate.
[5] A polyurethane obtained by the production method described in [4].

Advantageous Effects of Invention

According to the invention, a polyester polyol from which a polyurethane having excellent acid resistance and excellent alkali resistance can be produced can be provided. Also, a method for producing a polyurethane having excellent acid resistance and excellent alkali resistance and a polyurethane produced by the method can be provided.

DESCRIPTION OF EMBODIMENTS

The invention is explained in detail below.

The invention relates to a polyester polyol containing 1,3-propanediol having an alicyclic skeleton in a side chain, 3-methyl-1,5-pentanediol and a dibasic acid component as constituent components.

[Polyester Polyol]

As the dibasic acid component constituting the polyester polyol of the invention, a dibasic acid component which is used for a general polyester polyol can be used without any particular limitation. Examples thereof include: aliphatic dibasic acids such as succinic acid, glutaric acid, adipic acid, pimelic acid, suberic acid, azelaic acid, sebacic acid, dodecanedioic acid, brasylic acid and dimer acid; alicyclic dicarboxylic acids such as 1,4-cyclohexanedicarboxylic acid; aromatic dibasic acids such as phthalic acid, isophthalic acid, terephthalic acid and naphthalenedicarboxylic acid; and the like. Of these examples, adipic acid, azelaic acid, sebacic acid, terephthalic acid, isophthalic acid and naphthalenedicarboxylic acid are preferably used, taking into account the availability and the like. A kind of the dibasic acids may be used alone, or two or more kinds thereof may be used in combination.

The alicyclic skeleton of the 1,3-propanediol having an alicyclic skeleton in a side chain constituting the polyester polyol of the invention is not particularly limited, but an alicyclic skeleton having 3 to 10 carbon atoms is preferable. The number of the alicyclic skeleton(s) in the molecule may be one or may be two or more. Examples of specific compounds include cyclopropane-1,1-dimethanol, cyclobutane-1,1-dimethanol, cyclopentane-1,1-dimethanol, cyclohexane-1,1-dimethanol, 2-methylcyclohexane-1,1-dimethanol, 1-cyclohexene-4,4-dimethanol, cycloheptane-1,1-dimethanol, cyclooctane-1,1-dimethanol, dimethylcyclooctane-1,1-dimethanol and the like. Of these examples, cyclopentane-1,1-dimethanol, cyclohexane-1,1-dimethanol, 2-methylcyclohexane-1,1-dimethanol, 1-cyclohexene-4,4-dimethanol and the like are preferable, taking into account the availability and the like, and cyclohexane-1,1-dimethanol is particularly preferable. A kind of the compounds may be used alone, or two or more kinds thereof may be used in combination.

The mechanism of action is not fully clear, but it is speculated that when 1,3-propanediol having an alicyclic skeleton in a side chain and 3-methyl-1,5-pentanediol are used in combination, the presence of the alicyclic skeleton has an effect of protecting the ester bond, and a polyester polyol from which a polyurethane having excellent acid resistance and excellent alkali resistance can be produced can be obtained.

The use ratio of the 1,3-propanediol having an alicyclic skeleton in a side chain and the 3-methyl-1,5-pentanediol to be used is not particularly limited, but the ratio of use amount thereof is preferably in the range of 1/99 to 99/1 by molar ratio, more preferably in the range of 5/95 to 95/5 from the viewpoints of acid resistance and alkali resistance, further preferably in the range of 15/85 to 85/15.

The polyester polyol of the invention can also contain a polyhydric alcohol component (preferably a diol) other than the 1,3-propanediol having an alicyclic skeleton in a side chain and 3-methyl-1,5-pentanediol. As the other polyhydric alcohol component (preferably a diol), a polyhydric alcohol component (preferably a diol) which is used for a general polyester polyol can also be used. In general, the amount of the other polyhydric alcohol component (preferably a diol) is preferably 50 mol % or less based on the total amount of the 1,3-propanediol having an alicyclic skeleton in a side chain and 3-methyl-1,5-pentanediol, more preferably 30 mol % or less.

Taking into account the case in which the other polyhydric alcohol component (preferably a diol) is contained, the ratio of the total amount of the 1,3-propanediol having an alicyclic skeleton in a side chain and 3-methyl-1,5-pentanediol and the amount of the dibasic acid component, which are the constituent components of the polyester polyol of the invention, in terms of [(the number of constituent units derived from the 1,3-propanediol having an alicyclic skeleton in a side chain)+(the number of constituent units derived from 3-methyl-1,5-pentanediol)+(the number of constituent units derived from the other polyhydric alcohol component)]:(the number of constituent units derived from the dibasic acid component), is preferably in the range of 1.4:1 to 1.01:1, more preferably in the range of 1.2:1 to 1.04:1, further preferably 1.1:1 to 1.05:1.

The average molecular weight of the polyester polyol of the invention is not particularly limited but is preferably 300 to 4000, further preferably 350 to 3500, particularly preferably 450 to 3000. When the average molecular weight of the polyester polyol is 300 or more, the hydroxyl group concentration is diluted sufficiently, and gelation does not occur easily during the urethane formation. On the other hand, when the average molecular weight of the polyester polyol is 4000 or less, the viscosity in the dissolved state is low, and handling during the urethane formation becomes easy. In the invention, the average molecular weight means the number average molecular weight calculated from the hydroxyl value of the polyester polyol generated.

The polyester polyol of the invention preferably has a melting point of 25° C. or lower. The polyester polyol may be in the form of solid, wax, liquid or the like depending on the structure and the molecular weight, but the form of liquid is superior in view of handling because the time required for dissolution and the energy required for dissolution can be saved.

The alkali metal content of the polyester polyol of the invention is 20 ppm by mass or less, preferably 10 ppm by mass or less, more preferably 4 ppm by mass or less, further preferably 2 ppm by mass or less, particularly preferably 1.5 ppm by mass or less, most preferably 1 ppm by mass or less.

The method for producing the polyester polyol of the invention is not particularly limited. An example thereof is a production method in which a dibasic acid component is used as a starting material and is subjected to esterification or transesterification with 1,3-propanediol having an alicyclic skeleton in a side chain and 3-methyl-1,5-pentanediol.

The starting materials used for the esterification or the transesterification of a dibasic acid component or a dialkyl ester of a dibasic acid component, 1,3-propanediol having an alicyclic skeleton in a side chain and 3-methyl-1,5-pentanediol are explained below.

Examples of the dibasic acid component or the dialkyl ester of a dibasic acid component used in this reaction include: aliphatic dibasic acids such as succinic acid, glutaric acid, adipic acid, pimelic acid, suberic acid, azelaic acid, sebacic acid, dodecanedioic acid, brasylic acid and dimer acid or dialkyl esters of the dibasic acids such as dimethyl esters, diethyl esters, dipropyl esters and dibutyl esters; alicyclic dicarboxylic acids such as 1,4-cyclohexanedicarboxylic acid or dialkyl esters of the dibasic acids such as dimethyl esters, diethyl esters, dipropyl esters and dibutyl esters; aromatic dibasic acids such as phthalic acid, isophthalic acid, terephthalic acid and naphthalenedicarboxylic acid or dialkyl esters of the dibasic acids such as dimethyl esters, diethyl esters, dipropyl esters and dibutyl esters; and the like. Of these examples, adipic acid, azelaic acid, sebacic acid, terephthalic acid, isophthalic acid and naphthalenedicarboxylic acid or dialkyl esters of the dibasic acids are preferably used, taking into account the availability and the like. A kind of the dibasic acids or the dialkyl esters of dibasic acids may be used alone, or two or more kinds thereof may be used in combination.

As the 1,3-propanediol having an alicyclic skeleton in a side chain, the 1,3-propanediol having an alicyclic skeleton in a side chain described above can be used.

As 3-methyl-1,5-pentanediol, commercial products can be used.

The polyester polyol of the invention is obtained by esterification or transesterification of the dibasic acid component or the dialkyl ester of a dibasic acid component, the 1,3-propanediol having an alicyclic skeleton in a side chain and 3-methyl-1,5-pentanediol, which are described above as the starting materials. For the esterification or the transesterification, a method which is generally used for esterification or transesterification in organic synthesis reactions can be applied, and for example, a desired polyester polyol can be obtained by heating and condensing the dibasic acid component, the 1,3-propanediol having an alicyclic skeleton in a side chain and 3-methyl-1,5-pentanediol. The temperature of the esterification or the transesterification is generally 140 to 240° C., preferably 180 to 220° C. The color hue of the polyester polyol can be maintained excellent by sending an inert gas such as nitrogen or argon into the liquid during the reaction. The esterification or the transesterification may be conducted in the presence of a solvent which does not affect the reaction but in general is preferably conducted without any solvent.

The esterification or the transesterification is preferably conducted in the presence of a catalyst. Preferable catalysts are: titanium compounds such as tetrabutyl titanate, tetraisopropyl titanate, tetra-2-ethylhexyl titanate and titanium acetylacetonate; tin compounds such as dibutyltin oxide, methylphenyltin oxide and hexaethyltin oxide; and magnesium compounds such as magnesium carbonate, magnesium oxide and magnesium alkoxide. Titanium compounds such as tetrabutyl titanate, tetraisopropyl titanate, tetra-2-ethylhexyl titanate and titanium acetylacetonate are more preferable. The amount of the catalyst to be used is not particularly limited but in general is, in terms of the metal atoms based on the polyhydric alcohol(s), preferably in the range of 0.5 to 500 ppm by mass, more preferably in the range of 1 to 100 ppm by mass, particularly preferably 2 to 50 ppm by mass. When the amount of the catalyst is 0.5 ppm by mass or more, the polyester polyol can be generated rapidly, and the amount is economically advantageous because the period of time is shortened. On the other hand, when the amount of the catalyst is 500 ppm by mass or less, the catalyst can be easily removed or deactivated after the reaction.

The catalyst used for producing the polyester polyol also acts as a catalyst in the subsequent urethane formation reaction. Thus, in order to control the reactivity of the subsequent urethane formation reaction, the catalyst is desirably deactivated after the production of the polyester polyol, and the catalyst is desirably deactivated completely. As the method for deactivating the catalyst, a method for deactivating a catalyst used for the production of a general polyester polyol can be applied. For example, when a titanium compound is used as the catalyst, a method for deactivating the catalyst by adding water or a phosphorus compound, a method in which a phosphorus compound is further added after water is added and the like are used. Because the influence of the titanium compound can be reduced sufficiently, a method in which a phosphorus compound is further added after water is added is preferable.

The deactivation method for the case in which a titanium compound is used as the catalyst is explained below.

Heating with the addition of water for deactivating the catalyst is not particularly limited but is in general conducted preferably at a temperature of 70 to 120° C., particularly preferably at a temperature of 90 to 120° C. The heat treatment period is not particularly limited but is in general preferably about one to three hours.

Examples of the phosphorus compound to be added include phosphorous acid, phosphoric acid, dimethyl phosphite, diisopropyl phosphite, di-n-butyl phosphite, isobutyl phosphite, di-n-ethylhexyl phosphite, dilauryl phosphite, dioleyl phosphite, distearyl phosphite, diphenyl phosphite, monomethyl phosphite, monoethyl phosphite, dimethyl phosphate, diethyl phosphate, diisopropyl phosphate, di-n-butyl phosphate, isobutyl phosphate, di-n-ethylhexyl phosphate, dilauryl phosphate, dioleyl phosphate, distearyl phosphate, diphenyl phosphate, monomethyl phosphate, monoethyl phosphate and the like. Of these examples, phosphorous acid, diphenyl phosphite, distearyl phosphite and diphenyl phosphate are preferable.

With respect to the amount of the phosphorus compound to be added based on the amount of the titanium compound contained in the polyester polyol, the ratio by mole of titanium atoms in the titanium compound:phosphorus atoms in the phosphorus compound is preferably 1:0.01 to 2.

When the polyester polyol produced in the above manner is used as a starting material of a polyurethane, the polyester polyol produced in the above manner is preferably used after removing water from the polyester polyol. Water is removed preferably after the addition of the phosphorus compound, although the method is not limited thereto, and water may be removed after the heat treatment with the addition of water and before the addition of the phosphorus compound. Water can be removed by any method such as heating and drying at a reduced pressure.

The polyester polyol of the invention can be obtained in this manner.

[Production Method of Polyurethane]

The method for producing a polyurethane in the invention includes a step of reacting a polyester polyol and a polyisocyanate. The polyurethane of the invention is obtained by the production method.

When a polyurethane is produced using the polyester polyol of the invention, a method which is used for urethane formation reaction of a general polyester polyol can be applied. As the isocyanate, for example, generally used isocyanates such as diphenylmethane-4,4'-diisocyanate (hereinafter abbreviated to MDI), tolylene diisocyanate, 1,5-naphthalene diisocyanate, xylylene diisocyanate, isophorone diisocyanate, hexamethylene diisocyanate and hydrogenated MDI can be used. Also, a chain extender such as a low molecular polyol or polyamine and the like can be used together according to the need. The chain extender is not particularly limited, but a low molecular compound which mainly contains an aliphatic diol having 2 to 20 carbon atoms and which has at least two active hydrogen atoms (hereinafter sometimes simply referred to as "a low molecular compound having active hydrogen atoms") is preferably used. Examples of the low molecular compound having active hydrogen atoms include ethylene glycol, 1,3-propanediol, 1,4-butanediol, 1,5-pentanediol, 1,6-hexanediol, 3-methyl-1,5-pentanediol, 1,8-octanediol, 1,9-nonanediol, xylylene glycol, bis-hydroxy benzene, neopentyl glycol, trimethylolpropane, glycerin, 3,3-dichloro-4,4'-diaminodiphenylmethane, isophorone diamine, 4,4'-diaminodiphenylmethane and the like.

The polyurethane obtained by the above method has excellent hydrolysis resistance under acidic and basic conditions and can be used for uses such as sheets, films, forms, rolls, gears, solid tires, belts, hoses, tubes, packing materials, vibration proof materials, soles, sports shoes, machine parts, building materials, automotive parts, furniture, linings, sealing materials, waterproof materials, sporting goods, elastic fibers, artificial leather, fiber treating agents, adhesives, coating agents, binders and paints.

EXAMPLES

The invention is explained in further detail below by Examples, but the invention is not limited by the Examples. In the Examples and the Comparative Examples below, the physical property values were measured by the following methods.

(Measurement of Number Average Molecular Weight)

The hydroxyl value and the acid value of a polyester polyol obtained were measured in accordance with JIS K1557, and the number average molecular weight was determined by calculation based on the values obtained.

(Hydrolysis Resistance)

Into a test tube, 0.5 g of a polyester polyol and 10 ml of water were put, and the tube was sealed. After heating at 100° C. for 14 days, the liquid inside was taken out, and the amount of acids derived from the carboxyl groups generated by hydrolysis was analyzed by neutralization titration.

(Tensile Test)

A test piece of the dumbbell shape of JIS4 was produced from a polyurethane film having a thickness of 100 μm, and a tensile test was conducted using a universal tester (manufactured by Instron, type 3345) under the conditions of an air temperature of 25° C. and a humidity of 50% at a speed of testing rate of stressing of 50 cm/minute. Thus, the tensile strength at break and the elongation at break were measured.

(Evaluation of Acid Resistance)

A polyurethane film having a thickness of 100 μm and a 5 mass % aqueous sulfuric acid solution in an amount in which the entire polyurethane film was immersed were put in a container, and the container was sealed, followed by heating at 60° C. for 24 days. The tensile test was conducted using the polyurethane film after heating, and the ratio of the tensile strengths at break before and after heating was regarded as the strength retention.
(Evaluation of Alkali Resistance)

A polyurethane film having a thickness of 100 μm and a 5 mass % aqueous sodium hydroxide solution in an amount in which the entire polyurethane film was immersed were put in a container, and the container was sealed, followed by heating at 60° C. for 14 days. The tensile test was conducted using the polyurethane film after heating, and the ratio of the tensile strengths at break before and after heating was regarded as the strength retention.

Example 1 (Preparation of Polyester Polyol)

To a reactor, 142.4 g of adipic acid, 85.6 g of cyclohexane-1,1-dimethanol and 71.4 g of 3-methyl-1,5-pentanediol were charged, and the mixture was heated to 200° C. in a nitrogen atmosphere at the normal pressure. Esterification was thus conducted while water generated was distilled off from the system. At the point where the distillation of water generated became less, 5 mg of titanium tetraisopropoxide was added. The reaction was continued while reducing the pressure, and 3-methylpentanediol was distilled off. Next, the mixture was cooled, and the pressure was returned. Then, 5 g of water (corresponding to 2 mass % relative to the theoretical yield) was added, and the mixture was stirred at 100° C. for two hours. Water was distilled off at a reduced pressure. A polyester polyol having a number average molecular weight of 2125 was thus obtained. The hydrolysis resistance test was conducted using the polyester polyol obtained. The results obtained are shown in Table 1.

Examples 2 and 3 and Comparative Example 1 (Preparation of Polyester Polyols)

Condensation reaction was conducted in the same manner as in Example 1 except that the diol components and the dibasic acid component shown in Table 1 were used at the respective ratios by mole shown in Table 1, and the polyester polyols of Examples 2 and 3 and Comparative Example 1 were obtained. The number average molecular weights and the results of the hydrolysis resistance test are shown in Table 1.

TABLE 1

| | Diol Component | | Dibasic Acid Component | Number Average Molecular Weight | Hydrolysis Resistance mgKOH/g |
|---|---|---|---|---|---|
| | CHD*1 | MPD*2 | AA*3 | | |
| Example 1 | 50 | 50 | 100 | 2125 | 12 |
| Example 2 | 75 | 25 | 100 | 2004 | 11 |
| Example 3 | 25 | 75 | 100 | 2100 | 19 |
| Comparative Example 1 | | 100 | 100 | 2020 | 30 |

*1cyclohexane-1,1-dimethanol
*23-methyl-1,5-pentanediol
*3adipic acid

Example 4 (Production of Polyurethane Film and Evaluation of Physical Properties)

To a reactor, 40.0 g of the polyester polyol obtained in Example 1 (18.8 mmol; calculated from the number average molecular weight) and 3.9 g of 1,4-butanediol (37.7 mmol) were charged, and the mixture was stirred at 80° C. To the mixture, 15.5 g of 4,4'-diphenylmethane diisocyanate (62.1 mmol) was added, and the mixture was stirred for 1.5 minutes. The reaction solution was taken out onto a Teflon sheet and heated with a hot-air drier at 90° C. for 20 hours. The polyurethane obtained was dissolved in N,N'-dimethylformamide (abbreviated to DMF) in such a manner that the non-volatile component concentration became 25 mass %, and a DMF solution of the polyurethane was thus prepared. The DMF solution of the polyurethane obtained was flow casted on a glass plate and dried, and a polyurethane film having a thickness of 100 μm was obtained. Using this film, the acid resistance test and the alkali resistance test were conducted. The results are shown in Table 2.

Example 5 (Production of Polyurethane Film and Evaluation of Physical Properties)

A polyurethane film was produced in the same manner as in Example 4 except that the polyester polyol obtained in Example 2 was used, and the acid resistance test and the alkali resistance test were conducted. The results are shown in Table 2.

Example 6 (Production of Polyurethane Film and Evaluation of Physical Properties)

A polyurethane film was produced in the same manner as in Example 4 except that the polyester polyol obtained in Example 3 was used, and the acid resistance test and the alkali resistance test were conducted. The results are shown in Table 2.

Comparative Example 2 (Production of Polyurethane Film and Evaluation of Physical Properties)

A polyurethane film was produced in the same manner as in Example 4 except that the polyester polyol obtained in Comparative Example 1 was used, and the acid resistance test and the alkali resistance test were conducted. The results are shown in Table 2.

TABLE 2

| | Diol Component | | Dibasic Acid Component | Elongation at Break before Heating | Acid Resistance Test Strength Retention | Alkali Resistance Test Strength Retention |
|---|---|---|---|---|---|---|
| | CHD | MPD | AA | | | |
| Example 4 | 50 | 50 | 100 | 594% | 42% | 54% |
| Example 5 | 75 | 25 | 100 | 494% | 70% | 75% |
| Example 6 | 25 | 75 | 100 | 603% | 37% | 47% |
| Comparative Example 2 | | 100 | 100 | 565% | 26% | 17% |

From Table 1, the polyester polyols of the invention were superior in hydrolysis resistance to the polyester polyol containing 3-methyl-1,5-pentanediol. Also, from the results shown in Table 2, the polyurethanes obtained from the polyester polyols of the invention had equivalent flexibility to that of the polyurethane obtained from the polyester polyol containing 3-methyl-1,5-pentanediol and were superior in acid resistance and alkali resistance.

Although the invention has been explained in detail and referring to specific embodiments, it is obvious to one skilled in the art that various changes and modifications can be added without departing from the spirit and the scope of the invention.

This application is based on a Japanese patent application filed on Mar. 31, 2014 (patent application No. 2014-72677), and the contents thereof are incorporated herein by reference.

The invention claimed is:

1. A polyester polyol, comprising:
   1,3-propanediol having an alicyclic skeleton in a side chain, wherein the 1,3-propanediol having an alicyclic skeleton in a side chain is selected from the group consisting of cyclopropane-1,1-dimethanol, cyclobutane-1,1-dimethanol, cyclopentane-1,1-dimethanol, cyclohexane-1,1-dimethanol, 1-cyclohexene-4,4-dimethanol, cycloheptane-1,1-dimethanol, cyclooctane-1,1-dimethanol, and dimethylcyclooctane-1,1-dimethanol;
   3-methyl-1,5-pentanediol; and
   a dibasic acid component,
   as constituent components.

2. The polyester polyol according to claim 1, wherein a ratio of an amount of the 1,3-propanediol having an alicyclic skeleton in a side chain to the 3-methyl-1,5-pentanediol is from 1/99 to 99/1 by molar ratio.

3. The polyester polyol according to claim 1, wherein the 1,3-propanediol having an alicyclic skeleton in a side chain is cyclohexane-1,1-dimethanol.

4. A method for producing a polyurethane, comprising reacting the polyester polyol according to claim 1 and a polyisocyanate.

5. A polyurethane obtained by the production method according to claim 4.

6. The polyester polyol according to claim 2, wherein the 1,3-propanediol having an alicyclic skeleton in a side chain is cyclohexane-1,1-dimethanol.

7. A method for producing a polyurethane, comprising reacting the polyester polyol according to claim 2 and a polyisocyanate.

8. A polyurethane obtained by the production method according to claim 7.

9. A method for producing a polyurethane, comprising reacting the polyester polyol according to claim 3 and a polyisocyanate.

10. A polyurethane obtained by the production method according to claim 9.

11. The polyester polyol according to claim 1, further comprising a polyhydric alcohol component which is a diol, wherein a ratio of a total amount of the 1,3-propanediol having an alicyclic skeleton in a side chain, 3-methyl-1,5-pentanediol, and the polyhydric alcohol component to the amount of the dibasic acid component [(the number of constituent units derived from the 1,3-propanediol having an alicyclic skeleton in a side chain)+(the number of constituent units derived from 3-methyl-1,5-pentanediol)+(the number of constituent units derived from the other polyhydric alcohol component)]:(the number of constituent units derived from the dibasic acid component) is in the range of 1.4:1 to 1.01:1.

12. The polyester polyol according to claim 1, wherein the dibasic acid component is selected from the group consisting of adipic acid, azelaic acid, sebacic acid, terephthalic acid, isophthalic acid, naphthalenedicarboxylic acid, and dialkyl esters thereof.

* * * * *